US011076977B2

(12) United States Patent
He et al.

(10) Patent No.: US 11,076,977 B2
(45) Date of Patent: Aug. 3, 2021

(54) INDWELLING EVACUATOR FOR FECES

(71) Applicant: Jiangsu Hengai Medical Equipment Co., Ltd, Yancheng (CN)

(72) Inventors: Hang He, Shanghai (CN); Hanzhong He, Yancheng (CN)

(73) Assignee: JIANGSU HENGAI MEDICAL EQUIPMENT CO., LTD., Yancheng (CN)

( * ) Notice: Subject to any disclaimer, the term of this patent is extended or adjusted under 35 U.S.C. 154(b) by 371 days.

(21) Appl. No.: 16/319,232

(22) PCT Filed: Jul. 21, 2017

(86) PCT No.: PCT/CN2017/093897
§ 371 (c)(1),
(2) Date: Jan. 18, 2019

(87) PCT Pub. No.: WO2018/019185
PCT Pub. Date: Feb. 1, 2018

(65) Prior Publication Data
US 2019/0240060 A1 Aug. 8, 2019

(30) Foreign Application Priority Data

Jul. 24, 2016 (CN) .......................... 201610583265.8

(51) Int. Cl.
*A61F 5/44* (2006.01)
*A61B 17/22* (2006.01)
(Continued)

(52) U.S. Cl.
CPC ............ *A61F 5/4404* (2013.01); *A61B 17/22* (2013.01); *A61B 17/22012* (2013.01);
(Continued)

(58) Field of Classification Search
CPC ........ A61F 5/4404; A61F 5/442; A61F 5/451; A61B 17/22; A61B 17/22012; A61B 2017/22037
See application file for complete search history.

(56) References Cited

U.S. PATENT DOCUMENTS 2,691,373 A * 10/1954 Bried .................. A61M 3/0233
604/265
3,316,912 A * 5/1967 Whitaker ......... A61B 17/22031
606/1
(Continued)

FOREIGN PATENT DOCUMENTS

CN 201453432 U 5/2010
CN 102119878 A 7/2011
(Continued)

OTHER PUBLICATIONS

Written Opinion of the International Search Authority from corresponding PCT/CN2017/093897.
(Continued)

*Primary Examiner* — Benjamin J Klein
*Assistant Examiner* — Hans Kaliher
(74) *Attorney, Agent, or Firm* — Dragon Sun Law Firm, PC; Jinggao Li, Esq.

(57) ABSTRACT

An indwelling evacuator for feces, a stranding cage is disposed in a cylindrical main body, and a soft shaft is connected to the rear end of the stranding cage. Petaloid movable blades are hingedly connected to the front end of the cylindrical main body, and are in the shape of a bud when the petaloid movable blades are closed. A blocking ring is disposed on the outer wall of the cylindrical main body. A sliding ring member is disposed in the cylindrical main body to push the movable blades open to form an open space in the shape of a flower. The rear portion of the cylindrical main body is downward connected to a feces discharge hose.
(Continued)

In use, the bud portion in the front end is inserted into the anus, and the blocking ring limits the insertion depth.

5 Claims, 2 Drawing Sheets

(51) Int. Cl.
*A61F 5/442* (2006.01)
*A61F 5/451* (2006.01)

(52) U.S. Cl.
CPC .............. *A61F 5/442* (2013.01); *A61F 5/451* (2013.01); *A61B 2017/22037* (2013.01)

(56) References Cited

U.S. PATENT DOCUMENTS

| | | | | |
|---|---|---|---|---|
| 4,182,332 A | * | 1/1980 | Delaney | A61F 5/451 604/328 |
| 4,243,037 A | | 1/1981 | Smith et al. | |
| 5,000,750 A | * | 3/1991 | LeVeen | A61B 17/22 606/1 |
| 5,941,860 A | * | 8/1999 | Wheeler | A61F 5/451 604/327 |
| 2008/0033467 A1 | * | 2/2008 | Miyamoto | A61B 17/320725 606/180 |
| 2012/0289910 A1 | * | 11/2012 | Shtul | A61M 3/0216 604/267 |
| 2018/0064526 A1 | * | 3/2018 | Walzman | A61B 8/12 |

FOREIGN PATENT DOCUMENTS

| | | |
|---|---|---|
| CN | 203089471 U | 7/2013 |
| CN | 204863370 U | 12/2015 |

OTHER PUBLICATIONS

International Search Report from corresponding PCT/CN2017/093897.

* cited by examiner

INDWELLING EVACUATOR FOR FECES

CROSS REFERENCE TO RELATED APPLICATIONS

This application is the national phase entry of International Application No. PCT/CN2017/093897, filed on Jul. 21, 2017, which claims priority to Chinese application CN201610583265.8, filed on Jul. 24, 2016, the entire contents of which are incorporated herein by reference.

TECHNICAL FIELD

The invention refers to a nursing appliance, and relates to an indwelling evacuator for feces.

BACKGROUND

It is common for disabled elders to have fecal incontinence or lose the capability of independently discharging feces. Presently, the common approach for treating fecal incontinence is to wear diaper pants. However, it is obvious that diaper pants may result in body insanitation, and the body needs manual washing after discharging feces. It is difficult for the nursing work, because some nursing workers hate filth and awful smell. Certainly, in the first place, using diaper pants impairs self-esteem of the disabled people. Some conscious disabled people using diaper pants may diet to reduce discharging feces, and thus their health would be impacted. Similarly, the mental pressure also directly impacts their health situation. Some disabled people, especially suffering from dementia, loses capability of discharging, especially discharging feces. In this case, only manual method can offer assistance in discharging, and the usual method is that the nursing workers pick feces out by inserting fingers into the anus.

Nowadays, in the clinic or even at international or domestic medical appliance exhibitions, there is no appliance which can directly help people, who lost consciousness of independently discharging feces or have fecal incontinence, discharge feces whenever necessary. Most of appliances just receive induction information after discharging. Even if there are appliances which can dispose feces, these appliances require strict sealing, which may cause ulceration of skin where these appliances contact with.

As reading patent literatures, there are many international or domestic patent applications about feces evacuating appliances, for example, a device for the treatment of fecal impaction recited in U.S. Pat. No. 5,000,750A, a defecation assist device for constipation recited in CN201949054U. The common features of the two applications are that: the front portion enters into the rectum to fetch feces while the rear portion is a driving mechanism, and the front portion is connected to the rear portion rigidly. It is obviously difficult for the musculature, such as an anus, to bear the weight of the driving part and the working vibration. Furthermore, an approach should be provided to prevent the inner complicate structure of the rectum from touching an auger while allowing the auger to touch the feces.

It is desired for the disabled bed-ridden people having fecal incontinence and no capability of independently discharging feces, to have an indwelling evacuator for feces.

The objective of the disclosure is to provide an indwelling evacuator for feces which can easily be indwelled inside or outside of an anus, effectively protect the rectum, and keep the anus from bearing the weight of the driving mechanism and vibration when operating the driving mechanism. Meanwhile, the working procedure for evacuating feces can be designed via a controller.

SUMMARY

The objective of the disclosure is fulfilled as follows: An indwelling evacuator for feces, wherein an auger is disposed in a cylindrical main body, wherein a rear end of the auger penetrates through a rear wall of the cylindrical main body, a soft shaft joint is disposed at the rear end of the auger, the soft shaft joint is connected to a soft shaft, and the other end of the soft shaft is connected to a driving mechanism away from an anus; a sliding ring member is disposed in the cylindrical main body; a blocking ring is backward disposed on a front portion of an outer wall of the cylindrical main body; a plurality of petaloid movable blades are disposed at a front end of the cylindrical main body, and the plurality of petaloid movable blades are hingedly connected to the front end of the cylindrical main body; the petaloid movable blades are in the shape of a bud when the petaloid movable blades are closed; the sliding ring member contacts with a rear end of the petaloid movable blades when the sliding ring member is in a forward position; contact surfaces between the sliding ring member and the petaloid movable blades are complementary slopes or curve surfaces, and the petaloid movable blades are openable to form a shape of open flower; an inner surface of opened petaloid movable blades forms an open space in the shape of an open flower, a front portion of the auger is located in the open space; the surface, being toward a rectum wall, of the shape of the open flower forms a hemisphere curve surface having an outer diameter greater than an outer diameter of the cylindrical main body; meanwhile, the hemisphere curve surface and the blocking ring form a middle space around the cylindrical main body, clapping an anus sphincter from inside and outside of the anus; a rear portion of the cylindrical main body is downward connected to a feces discharge hose.

The petaloid movable blades are of mesh structure.

The sliding ring member is disposed in the cylindrical main body, and a pulling stick is disposed on an outer wall of the sliding ring member, and the pulling stick penetrates through the cylindrical main body and is fixed by a fastener.

A liquid pipe is disposed between the cylindrical main body and the sliding member, a rear end of the liquid pipe penetrates through the cylindrical main body, a front end of the liquid pipe has an opening in a cavity of the open petaloid movable blades, and the rear end of the liquid pipe is connected to a liquid inlet.

An indwelling evacuator for feces, an auger is disposed in a cylindrical main body. A soft shaft joint is disposed at the rear end of the auger, which penetrates through the rear wall of the cylindrical main body. The soft shaft joint is connected to the soft shaft, and the other end of the soft shaft is connected to a driving mechanism which is away from the anus. The sliding ring member is disposed in the cylindrical main body; the blocking ring is disposed backward on the front portion of the outer wall of the cylindrical main body; a plurality of petaloid movable blades, are disposed at the front end of cylindrical main body and hingedly connected to the front end of the cylindrical main body; the petaloid movable blades are in the shape of a bud when the petaloid movable blades are closed; the front portion of the shape of bud is a curve surface, which can facilitate entering into the anus during feces evacuation. The sliding ring member contacts with the rear end of the petaloid movable blades when the sliding ring member is in a forward position, and the contact surfaces between the sliding ring member and the petaloid movable blades are complementary slopes or curve surfaces by which the petaloid movable blades can be pushed open to form a shape of open flower; the inner surface of the pushed open petaloid movable blades forms an open space in the shape of an open flower, and the front portion of the auger extends outside of the front portion of the cylindrical main body and extends into an open space of a flower shape formed by the pushed open petaloid movable blades, which effectively prevents the contact between the auger and the rectum wall. The surface (toward the rectum wall) of a flower shape formed by the pushed open petaloid movable blades, forms a hemisphere curve surface having an outer diameter greater than the outer diameter of the cylindering body to better protect the rectum; meanwhile, the hemisphere curve surface and the blocking ring form a middle space around the cylindrical main body, clapping the anus sphincter from inside and outside of the anus, which effectively keeps the front end of the indwelling evacuator for feces from entering into the rectum limitlessly and prevents the indwelling evacuator for feces from sliding out of the anus when indwelling is required; the rear portion of the cylindrical main body is downward connected to a feces discharge hose.

As the soft shaft is connected to the auger, the driving mechanism can be kept away from the anus. The structure for evacuating feces can be easily inserted into the anus and fixed after the insertion, meanwhile the weight of the structure is reduced; the soft shaft only passes rotational power and does not pass the vibration brought by operating the power machine, which can effectively prevent the possible damage to the anus and rectus due to the vibration produced during operation of the power machine.

The petaloid movable blades are of mesh structure, which facilitates, the feces between the back of the open flower and the rectum, entering into the open flower and being evacuated.

The sliding ring member is disposed in the cylindrical main body, and a pulling stick is disposed on the outer wall of the sliding ring member. The pulling stick penetrates through the cylindrical main body and can be fixed by a fastener.

The liquid pipe is disposed between the cylindrical main body and the sliding member. The rear end of the pipe penetrates through the cylindrical main body and the front end of the pipe has an opening in a cavity of the pushed open petaloid movable blades. The rear end of the pipe is connected to the liquid inlet.

In use, the bud at the front end of the indwelling evacuator for feces is inserted into the anus, and the blocking ring limits the insertion depth. The pulling stick out of the cylindrical main body is pushed and fixed, and the front end of the sliding ring member drives the rear end of the petaloid movable blades which rotate around the axis to open the bud. After the bud is open, the indwelling evacuator is fixed in the anus. The soft shaft is connected to the soft shaft joint of the auger out of the cylindrical main body of the indwelling evacuator for feces. The soft shaft is driven, and the auger is rotated to discharge the feces. Warm water or other lubricant sprayed from the liquid pipe facilitates evacuating feces when necessary.

Indwelling the feces evacuator is important in nursing work for a patient having fecal incontinence. With the control system of the driving mechanism, the auger working at regular intervals can totally prevent from dirtying underwear and bed and increasing the nursing burden due to fecal incontinence. For disabled people who have no capability of discharging the feces, indwelling can reduce the frequency of inserting or pulling out the evacuator.

As to the indwelling evacuator for feces of the disclosure, the auger in the cylindrical main body is remotely driven by a soft shaft, so that the sizes of the evacuator indwelled inside and outside of the anus are very small and the weight is very light. More importantly, the soft shaft only passes rotational power and does not pass the vibration produced during operation of the power machine, which can effectively prevent the damage to the anus and rectus due to the vibration produced during operation of the power machine. The indwelling evacuator for feces has a structure which ensures that the evacuator can be easily indwelled, without injuring the anus and the rectum. The cost of the portion in front of the soft shaft is very low, so that the evacuator may be disposable after use. The implanting or indwelling operations inside and outside of the anus and the rectum are very simple and convenient. Accordingly, the feces problem of a bed-ridden patient having fecal incontinence or no capability of discharging the feces, especially the disabled elders, can be effectively resolved, the sanitation and the comfort of the patient can be improved, and the nursing burden can be thus reduced.

DETAILED DESCRIPTION OF THE INVENTION

Figure 1:
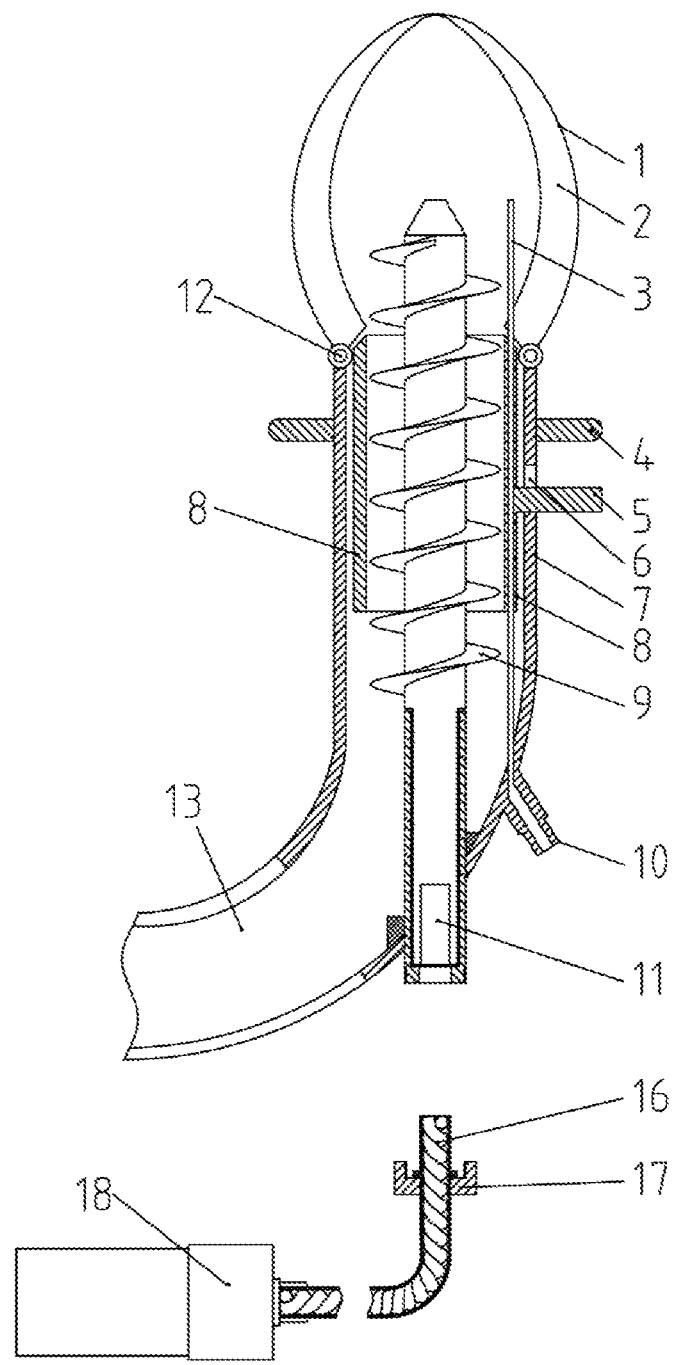
FIG. 1 is a structural view of the indwelling evacuator for feces when the front blades are closed.
Figure 2:
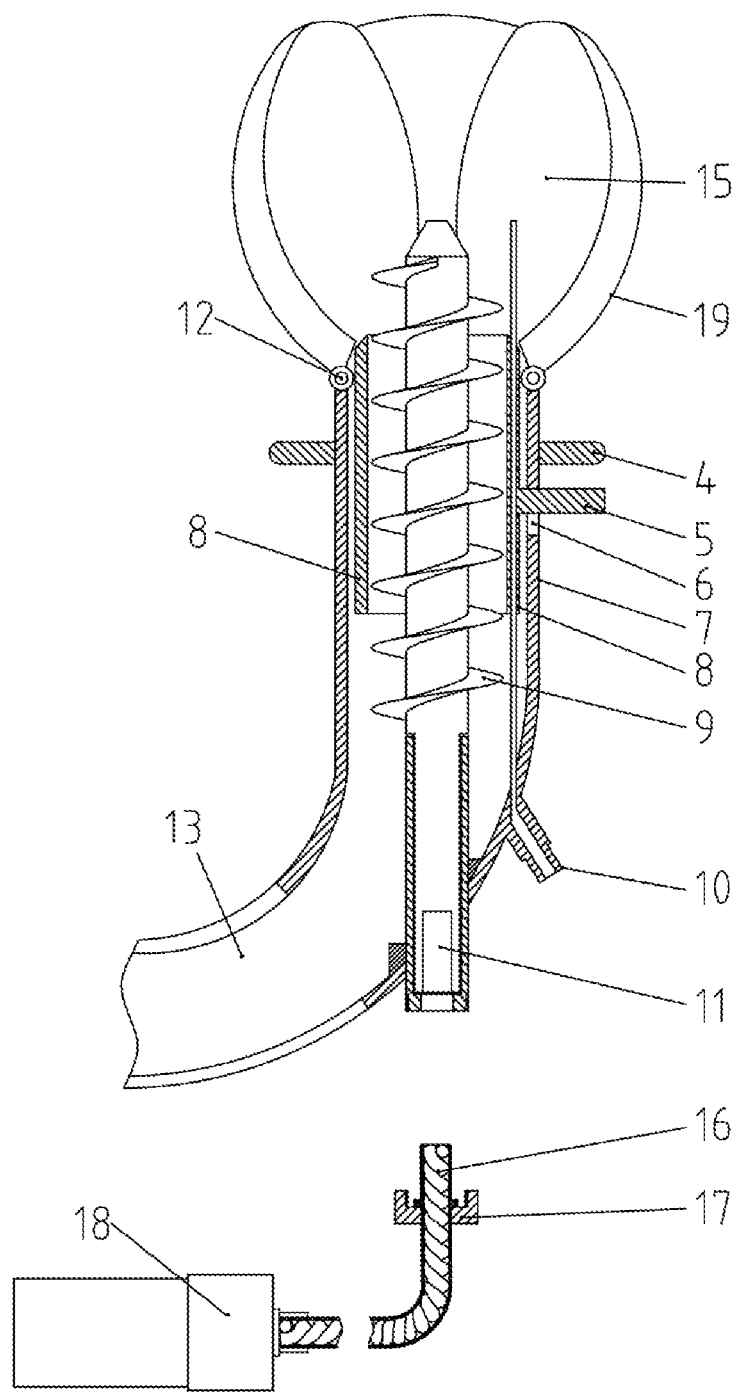
FIG. 2 is a structural view of the indwelling evacuator for feces when the front blades are opened.

Referring to FIGS. 1 and 2, as one of the embodiments of the disclosure, an indwelling evacuator for feces, an auger 9 is disposed in a cylindrical main body 7. A soft shaft joint 11 is disposed at the rear end of the auger 9, which penetrates through the rear wall of the cylindrical main body 7. The soft shaft joint 11 is connected to the soft shaft 16, and the other end of the soft shaft 16 is connected to 18 which is away from the anus. The sliding ring member 8 is disposed in the cylindrical main body 7; the blocking ring 4 is disposed backward on the front portion of the outer wall of the cylindrical main body 7; a plurality of petaloid movable blades 2, are disposed at the front end of cylindrical main body 7 and hingedly connected to the front end of the cylindrical main body 7; the petaloid movable blades 2 are in the shape of a bud 1 when the petaloid movable blades 2 are closed; the front portion of the shape of bud 1 is a curve surface, which can facilitate entering into the anus during feces evacuation. The sliding ring member 8 contacts with the rear end of the petaloid movable blades 2 when the sliding ring member 8 is in a forward position, and the contact surfaces between the sliding ring member 8 and the petaloid movable blades 2 are complementary slopes or curve surfaces by which the petaloid movable blades can be pushed open to form a shape of open flower 15; the inner surface of the pushed open petaloid movable blades 2 forms an open space in the shape of an open flower 15, and the front portion of the auger 9 extends outside of the front portion of the cylindrical main body 7 and extends into an open space of a flower shape 15 formed by the pushed open petaloid movable blades 2, which effectively prevents the contact between the auger 9 and the rectum wall. The surface (toward the rectum wall) of a flower shape 15 formed by the pushed open petaloid movable blades 2, forms a hemisphere curve surface 19 having an outer diameter greater than the outer diameter of the cylindering body 7 to better protect the rectum; meanwhile, the hemisphere curve surface 19 and the blocking ring 4 form a middle space around the cylindrical main body 7, clapping the anus sphincter from inside and outside of the anus, which effectively keeps the front end of the indwelling evacuator for feces from entering into the rectum limitlessly and prevents the indwelling evacuator for feces from sliding out of the anus when indwelling is required; the rear portion of the cylindrical main body 7 is downward connected to a feces discharge hose 13.

As the soft shaft 16 is connected to the auger 9, the driving mechanism 18 can be kept away from the anus. The structure for evacuating feces can be easily inserted into the anus and fixed after the insertion, meanwhile the weight of the structure is reduced; the soft shaft 16 only passes rotational power and does not pass the vibration brought by operating the power machine, which can effectively prevent the possible damage to the anus and rectus due to the vibration produced during operation of the power machine.

The petaloid movable blades 2 are of mesh structure, which facilitates, the feces between the back of the open flower 15 and the rectum, entering into the open flower and being evacuated.

The sliding ring member 8 is disposed in the cylindrical main body 7, and a pulling stick 5 is disposed on the outer wall of the sliding ring member 8. The pulling stick 5 penetrates through the cylindrical main body 7 and can be fixed by a fastener 6.

The liquid pipe 3 is disposed between the cylindrical main body 7 and the sliding member 8. The rear end of the pipe 3 penetrates through the cylindrical main body 7 and the front end of the pipe 3 has an opening in a cavity of the pushed open petaloid movable blades 2. The rear end of the pipe 3 is connected to the liquid inlet 10.

In use, the bud 1 at the front end of the indwelling evacuator for feces is inserted into the anus, and the blocking ring 4 limits the insertion depth. The pulling stick 5 out of the cylindrical main body 7 is pushed and fixed, and the front end of the sliding ring member 8 drives the rear end of the petaloid movable blades 2 which rotate around the axis 12 to open the bud 1. After the bud 1 is open, the indwelling evacuator is fixed in the anus. The soft shaft 16 is connected to the soft shaft joint 11 of the auger 9 out of the cylindrical main body 7 of the indwelling evacuator for feces. The soft shaft 16 is driven and the auger 9 is rotated to discharge the feces. Warm water or other lubricant sprayed from the liquid pipe 3 facilitates evacuating feces when necessary.

Indwelling the feces evacuator is important in nursing work for a patient having fecal incontinence. With the control system of the driving mechanism, the auger working at regular intervals can totally prevent from dirtying underwear and bed and increasing the nursing burden due to fecal incontinence. For disabled people who have no capability of discharging the feces, indwelling can reduce the frequency of inserting or pulling out the evacuator.

As to the indwelling evacuator for feces of the disclosure, the auger in the cylindrical main body is remotely driven by a soft shaft, so that the sizes of the evacuator indwelled inside and outside of the anus are very small and the weight is very light. More importantly, the soft shaft only passes rotational power and does not pass the vibration produced during operation of the power machine, which can effectively prevent the damage to the anus and rectus due to the vibration produced during operation of the power machine.

What is claimed is:

1. An indwelling evacuator for feces, comprising:
a cylindrical main body;
an auger;
wherein the auger is disposed in the cylindrical main body, wherein a rear end of the auger penetrates through a rear wall of the cylindrical main body,
a soft shaft joint is disposed at the rear end of the auger, the soft shaft joint is connected to an end of a soft shaft, and the other end of the soft shaft is connected to a driving mechanism;
a sliding ring member is disposed in the cylindrical main body; a blocking ring is disposed on a front portion of an outer wall of the cylindrical main body;
a plurality of movable blades are disposed at a front end of the cylindrical main body, and the plurality of movable blades are hingedly connected to the front end of the cylindrical main body;
the sliding ring member contacts with a rear end of the movable blades when the sliding ring member is in a forward position;
contact surfaces between the sliding ring member and the movable blades are complementary slopes or curve surfaces, and the movable blades are openable;
an inner surface of opened movable blades forms an open space, a front portion of the auger is located in the open space;
an outer surface of the opened movable blades forms a hemisphere curve surface having an outer diameter greater than an outer diameter of the cylindrical main body;
the hemisphere curve surface and the blocking ring form a middle space around the cylindrical main body;
a rear portion of the cylindrical main body is connected to a feces discharge hose.

2. The indwelling evacuator for feces according to claim 1, wherein the movable blades are of mesh structure.

3. The indwelling evacuator for feces according to claim 1, wherein the sliding ring member is disposed in the cylindrical main body, and a pulling stick is disposed on an outer wall of the sliding ring member, and the pulling stick penetrates through the cylindrical main body and is fixed by a fastener.

4. The indwelling evacuator for feces according to claim 1, wherein a liquid pipe is disposed between the cylindrical main body and the sliding member, a rear end of the liquid pipe penetrates through the cylindrical main body, a front end of the liquid pipe has an opening in a cavity of the open movable blades, and the rear end of the liquid pipe is connected to a liquid inlet.

5. An indwelling evacuator for feces, comprising:
a cylindrical main body;
an auger;
wherein the auger is disposed in the cylindrical main body, wherein a rear end of the auger penetrates through a rear wall of the cylindrical main body,
a soft shaft joint is disposed at the rear end of the auger, the soft shaft joint is connected to an end of a soft shaft, and the other end of the soft shaft is connected to a driving mechanism;
a sliding ring member is disposed in the cylindrical main body; a blocking ring is disposed on a front portion of an outer wall of the cylindrical main body;
a plurality of movable blades are disposed at a front end of the cylindrical main body, and the plurality of movable blades are hingedly connected to the front end of the cylindrical main body;

the sliding ring member contacts with a rear end of the movable blades when the sliding ring member is in a forward position;
contact surfaces between the sliding ring member and the movable blades are complementary slopes or curve surfaces, and the movable blades are openable;
an inner surface of opened movable blades forms an open space, a front portion of the auger is located in the open space;
an outer surface of the opened movable blades forms a hemisphere curve surface having an outer diameter greater than an outer diameter of the cylindrical main body;
the hemisphere curve surface and the blocking ring form a middle space around the cylindrical main body;
a rear portion of the cylindrical main body is connected to a feces discharge hose;
the movable blades are of mesh structure;
the sliding ring member is disposed in the cylindrical main body, and a pulling stick is disposed on an outer wall of the sliding ring member, and the pulling stick penetrates through the cylindrical main body and is fixed by a fastener;
a liquid pipe is disposed between the cylindrical main body and the sliding member, a rear end of the liquid pipe penetrates through the cylindrical main body, a front end of the liquid pipe has an opening in a cavity of the open movable blades, and the rear end of the liquid pipe is connected to a liquid inlet.

\* \* \* \* \*